(12) United States Patent
Gottlieb et al.

(10) Patent No.: US 8,845,727 B2
(45) Date of Patent: Sep. 30, 2014

(54) INTERVERTEBRAL BODY FUSION IMPLANT DEVICE

(75) Inventors: Jamie Gottlieb, Granger, IN (US); David Janice, Austin, TX (US)

(73) Assignee: Omni Acquisitions, Inc., Marietta, GA (US)

( * ) Notice: Subject to any disclaimer, the term of this patent is extended or adjusted under 35 U.S.C. 154(b) by 232 days.

(21) Appl. No.: 13/068,186

(22) Filed: May 4, 2011

(65) Prior Publication Data

US 2012/0283834 A1 Nov. 8, 2012

(51) Int. Cl.
*A61F 2/44* (2006.01)
*A61F 2/30* (2006.01)

(52) U.S. Cl.
CPC ....... *A61F 2/442* (2013.01); *A61F 2002/30884* (2013.01); *A61F 2002/4475* (2013.01); *A61F 2002/30774* (2013.01); *A61F 2002/30777* (2013.01); *A61F 2002/30785* (2013.01); *A61F 2/4465* (2013.01); *A61F 2002/30879* (2013.01); *A61F 2002/30904* (2013.01)
USPC .................................. 623/17.11; 623/17.16

(58) Field of Classification Search
CPC ....................................................... A61F 2/447
USPC ........................................................ 623/17.16
See application file for complete search history.

(56) References Cited

U.S. PATENT DOCUMENTS

| | | | |
|---|---|---|---|
| 6,592,624 B1 * | 7/2003 | Fraser et al. | 623/17.16 |
| 6,723,126 B1 * | 4/2004 | Berry | 623/17.11 |
| 7,060,097 B2 * | 6/2006 | Fraser et al. | 623/17.11 |
| 7,488,330 B2 * | 2/2009 | Stad | 606/102 |
| 7,806,933 B2 * | 10/2010 | Sears et al. | 623/17.11 |
| 7,887,592 B2 * | 2/2011 | Koske | 623/17.15 |
| D650,481 S * | 12/2011 | Gottlieb et al. | D24/155 |
| 8,083,796 B1 * | 12/2011 | Raiszadeh et al. | 623/17.11 |
| 8,206,449 B2 * | 6/2012 | Jansen et al. | 623/17.16 |
| 8,216,314 B2 * | 7/2012 | Richelsoph | 623/17.15 |
| 8,382,843 B2 * | 2/2013 | Laurence et al. | 623/17.16 |
| 2005/0149193 A1 * | 7/2005 | Zucherman et al. | 623/17.11 |
| 2006/0041313 A1 * | 2/2006 | Allard et al. | 623/17.15 |
| 2006/0116766 A1 * | 6/2006 | Lemaire | 623/17.11 |
| 2010/0204796 A1 * | 8/2010 | Bae et al. | 623/17.16 |

FOREIGN PATENT DOCUMENTS

WO WO9723175 * 7/1997

* cited by examiner

*Primary Examiner* — David Bates
(74) *Attorney, Agent, or Firm* — David O. Simmons

(57) ABSTRACT

An intervertebral body fusion implant device configured for being engaged between two adjacent vertebrae comprises an implant device body having an upper bone engaging portion and a lower bone engaging portion, a plurality of protrusions extending from each one of the upper and lower bone engaging portions, and a guide rail extending from each one of the bone engaging portions. A passage extends between the upper bone engaging portion and the lower bone engaging portion. The guide rail of each one of the bone engaging portions extends beyond a tip portion of each one of the protrusions thereof. Each one of the guide rails extends substantially parallel with each other one of the guide rails.

20 Claims, 2 Drawing Sheets

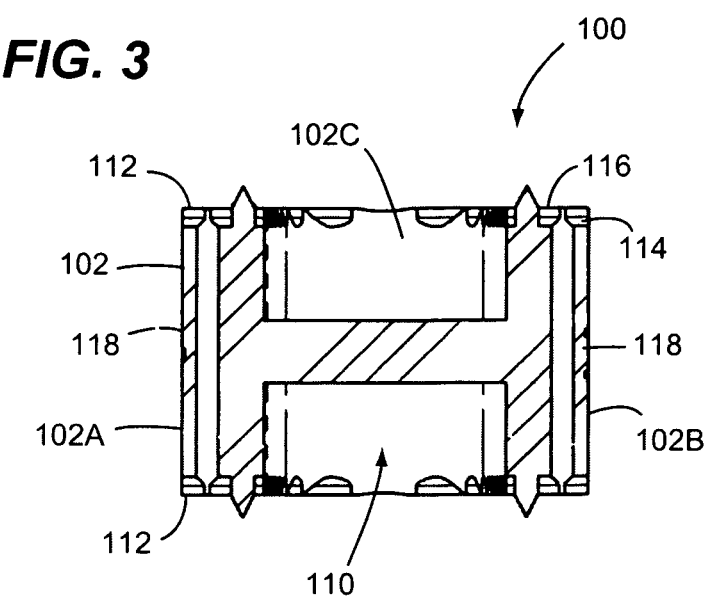
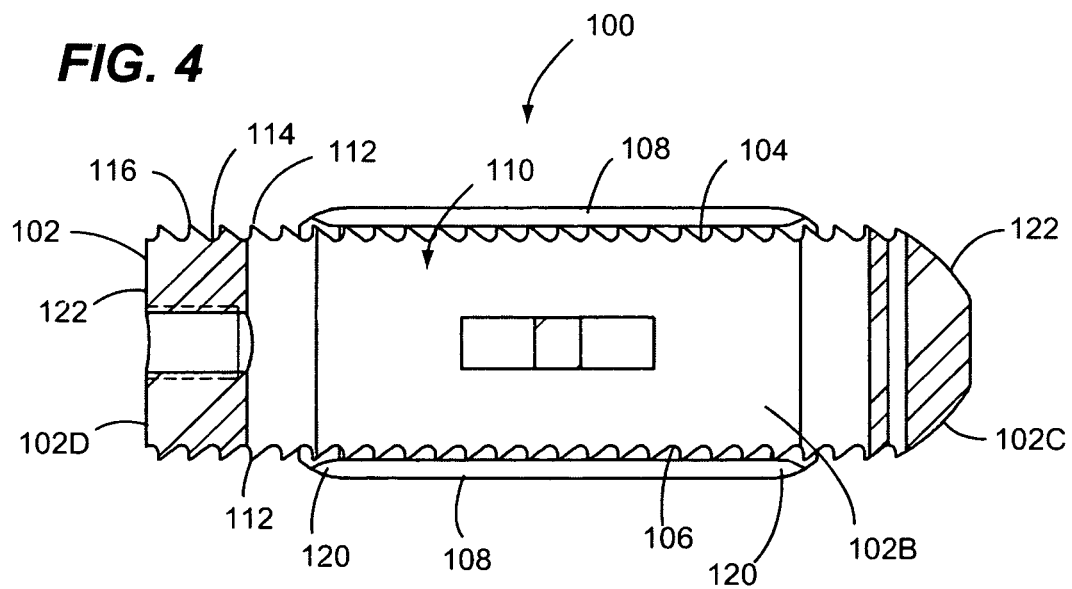

INTERVERTEBRAL BODY FUSION IMPLANT DEVICE

FIELD OF THE DISCLOSURE

The disclosures made herein relate generally intervertebral body fusion and, more particularly, to intervertebral body fusion implant device in the form of a cage, a spacer, and the like.

BACKGROUND

The spinal column is a biomechanical structure composed primarily of ligaments, muscles, vertebrae, and intervertebral disks. The biomechanical functions of the spine are numerous. One such function is providing for support of the body, which involves the transfer of the weight and the bending movements of the head, trunk and arms to the pelvis and legs. Another such function is providing for complex physiological motion between these parts. Still another such function is providing for protection of the spinal cord and nerve roots.

Removal of an intervertebral disc is often desired if and when the disc degenerates. The surgical treatment of those degenerative conditions of the spine in which the spinal disks are in various states of collapse commonly involves spinal fusion, that is, the joining together of adjacent vertebrae through an area of shared bone. To this end, the disc is replaced with an intervertebral body fusion implant device that maintains proper spacing between and orientation of two adjacent vertebrae. When the shared bone extends across the area previously occupied by the intervertebral disk, the fusion is referred to as an "interbody fusion." Fusion results in formation of a solid bony mass between adjacent vertebral bodies. The newly formed bony mass can assume a weight-bearing function and thereby relieve mechanical pain caused by an unstable degenerative disk. The bony fusion mass further can prevent long-term disk collapse or additional degenerative changes.

Interbody fusion of two adjacent vertebral bodies takes place over time. Accordingly, it is important for an intervertebral body fusion implant device positioned between two adjacent vertebral bodies to not only be accurately placed during initial placement, but to also maintain such position until interbody fusion is complete. Therefore, an intervertebral body fusion implant device is configured in a manner that allows for accurately placed during initial placement and for maintaining such position until fusion is complete is advantageous, desirable and useful.

SUMMARY OF THE DISCLOSURE

Embodiments of the present invention relate to intervertebral body fusion implant devices used in accomplishing interbody fusion of two adjacent vertebrae of a spine. More specifically, an intervertebral body fusion implant device configured in accordance with the present invention provides for accurate positioning during its initial placement and for maintaining such position until interbody fusion is complete. In doing so, an intervertebral body fusion implant device configured in accordance with an embodiment of the present invention advantageously overcome one or more shortcomings associated with prior art intervertebral body fusion implant devices.

In one embodiment of the present invention, an intervertebral body fusion implant device configured for being engaged between two adjacent vertebrae comprises an implant device body having an upper bone engaging portion and a lower bone engaging portion. The intervertebral body fusion implant device further comprises a guide rail extending from each one of the bone engaging portions. A passage extends through the implant device body between the upper bone engaging portion and the lower bone engaging portion. The upper and lower bone engaging portions each include a bone gripping structure configured for limiting relative movement between the implant device body and an engaged one of the adjacent vertebrae. The guide rail of each one of the bone engaging portions is exposed above an uppermost portion of the bone gripping structure thereof Each one of the guide rails extends substantially parallel with each other one of the guide rails.

In another embodiment of the present invention, an intervertebral body fusion implant device configured for being engaged between two adjacent vertebrae comprises an implant device body having an upper bone engaging portion and a lower bone engaging portion, a plurality of protrusions extending from each one of the upper and lower bone engaging portions, and a guide rail extending from each one of the bone engaging portions. A passage extends between the upper bone engaging portion and the lower bone engaging portion. The guide rail of each one of the bone engaging portions extends beyond a tip portion of each one of the protrusions thereof Each one of the guide rails extends substantially parallel with each other one of the guide rails.

In another embodiment of the present invention, an intervertebral body fusion implant device configured for being engaged between two adjacent vertebrae comprises first and second side walls each including an upper bone engaging portion and a lower bone engaging portion, a plurality of protrusions extending from the upper and lower bone engaging portions of each one of the side walls, first and second end walls connected between the first and second side walls in a manner providing a passage extending between the upper bone engaging portion of the first and second side walls and the lower bone engaging portion of the side walls, and a guide rail extending from each one of the bone engaging portions of each one of the side walls. The guide rail of each one of the bone engaging portions extends beyond a tip portion of each one of the protrusions thereof. The guide rail of each one of the bone engaging portions extends substantially parallel with the guide rail of each other one of the bone engaging portions.

These and other objects, embodiments, advantages and/or distinctions of the present invention will become readily apparent upon further review of the following specification, associated drawings and appended claims.

BRIEF DESCRIPTION OF THE DRAWINGS

FIG. 3 is a cross-sectional view taken along the line 3-3 in FIG. 1; and

FIG. 4 is a cross-sectional view taken along the line 4-4 in FIG. 1

DETAILED DESCRIPTION

Figure 1:
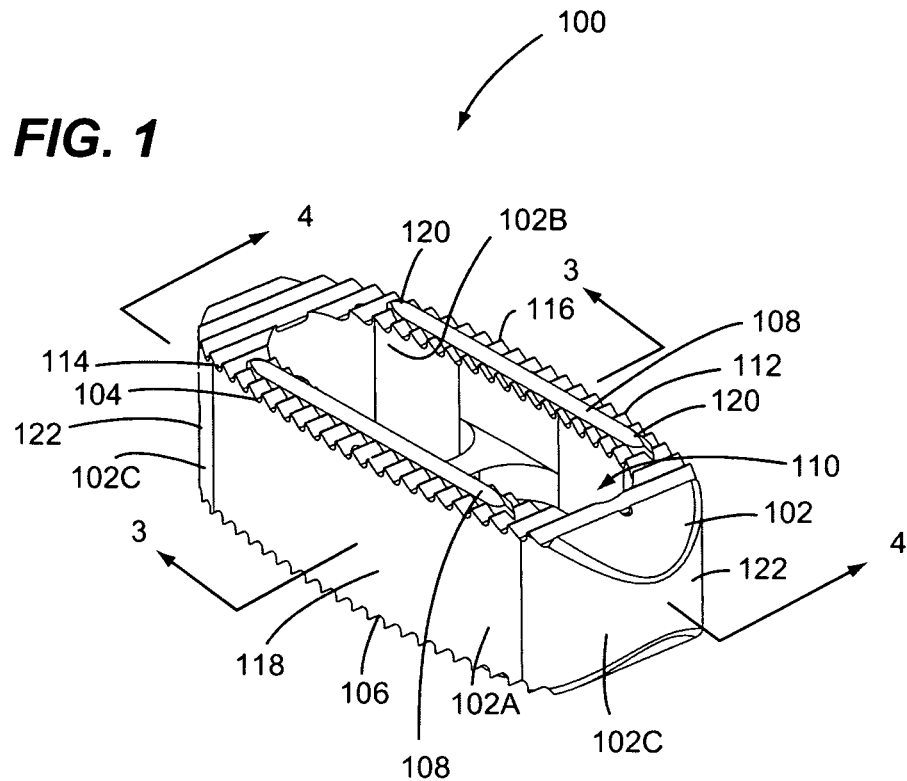
FIG. 1 is a perspective view showing an intervertebral body fusion implant device in accordance with an embodiment of the present invention.
Figure 2:
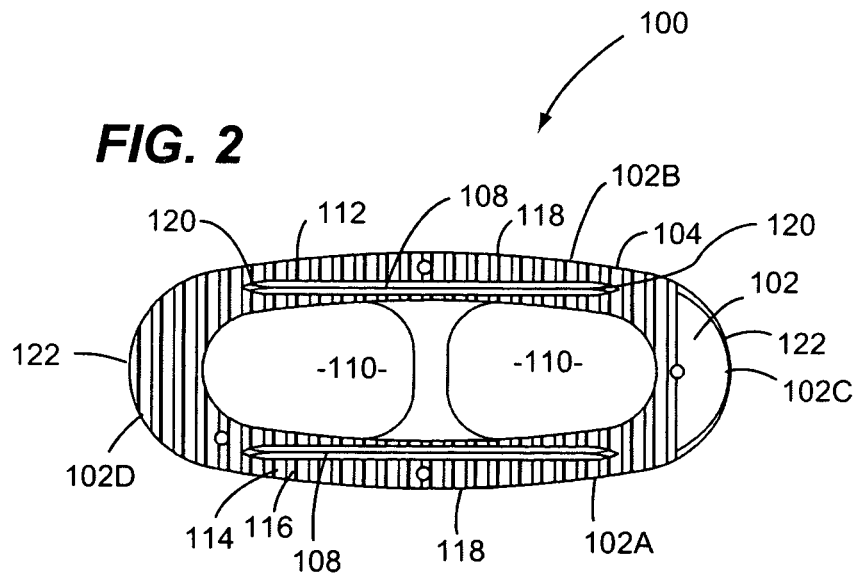
FIG. 2 is plan view of the intervertebral body fusion device shown in FIG. 1.

FIGS. 1-4 show various aspects of an intervertebral body fusion implant device 100 (i.e., the device 100) configured in accordance with an embodiment of the present invention. The device 100 is suitably configured for use in accomplishing interbody fusion of two adjacent vertebrae of a spine. Advantageously, the device 100 is configured in a manner that provides for accurate positioning during its initial placement and for maintaining such position until interbody fusion is complete. In doing so, the device 100 advantageously overcomes shortcomings associated with prior art intervertebral body fusion implant devices.

The device 100 includes an implant device body 102 having an upper bone engaging portion 104 and a lower bone engaging portion 106 and having a guide rail 108 extending from each one of the bone engaging portions 104, 106. A passage 110 extends through the implant device body 102 between the upper bone engaging portion 102 and the lower bone engaging portion 104. Preferably, but not necessarily, the guide rails 108 are integral with (e.g., unitary molded with) the implant device body 102.

The implant device body 102 includes a first side wall 102A, a second side wall 102B, a first end wall 102C and a second end wall 102D. The first end wall 102C and the second end wall 102D are connected between the first side wall 102A and the second side wall 102B at opposing end portions thereof in a manner providing the passage 110 extending between the upper bone engaging portion 104 and the lower bone engaging portion 106. The side walls 102A, 102B and the end walls 102C, 102D jointly define the upper bone engaging portion 104 and the lower bone engaging portion 106.

The upper and lower bone engaging portions 102, 104 each include a plurality of teeth 112 configured for limiting relative movement between the implant device body and an engaged one of the adjacent vertebrae. The teeth 112 are integral with and extend from the respective bone engaging portion 102, 104. A valley 114 is defined between adjacent ones of the teeth 112 and a ridge 116 is defined at a tip portion of each one of the teeth 112. Preferably, but not necessarily, the ridges 116 of all of the teeth 112 extend substantially parallel to each other. The teeth 112 are examples of protrusions that serve as bone gripping structure that are suitably configured for gripping an endplate of a vertebrae. It is disclosed herein that protrusions of other configurations, shapes, etc can be used in place of or in combination with the teeth 112.

The guide rail 108 of each one of the bone engaging portions 102, 104 is exposed above a tip portion of each one of the teeth 112 (i.e., an uppermost portion of the bone gripping structure) of the corresponding one of the bone engaging portions 102, 104. Preferably, but not necessarily, all of the guide rails 108 are substantially straight and extends substantially parallel with each other. Furthermore, the ridge 116 of each one of the teeth 112 preferably extends substantially perpendicular to each one of the guide rails 108.

Advantageously, each one of the guide rails is inwardly offset away from an adjacent exterior side face 118 of the implant device body 102 whereby a space is provided between each one of the guide rails 108 and the adjacent exterior side face 118 of the implant device body 102. A length of the implant device body 102 is substantially greater than a length of each one of the guide rails 108 and each one of the guide rails 108 is positioned such that a space is provided between end portions 120 of each one of the guide rails 108 and an adjacent end face 122 of the implant device body 102.

There are several aspects of the device 100 that provide advantageous and beneficial results. Certain ones of these aspects are directly related to the guide rails 108 and their associated construction and utility. As such, an intervertebral body function implant device having guide rails configured in accordance with the present invention offers advantageous and beneficial results.

One advantageous and beneficial result of the guide rail 108 is that, upon insertion of the device 100, the guide rails 108 engage the endplate of inferior and superior vertebral bodies (i.e., adjacent vertebrae bodies) preventing medial/lateral migration in a transverse placement or anterior/posterior migration in a lateral placement. The device 100 accomplishes this by creating a "track" in the each one of the endplates for the guide rails 108 to follow. This track following functionality allows a surgeon to accurately control placement of the device 100 instead of being forced to conform to a patient's individual anatomy. This is especially useful in cases where surgical access is limited, and there is a need to have more precise control of the implant to avoid vasculature and neural structures. It is also highly useful in instances where a disc space in which the device 100 is being placed has a large angulation due to degeneration, trauma or deformity that would force the device 1200 to migrate toward the more open portion of the disc space.

Another such advantageous and beneficial result of the guide rail 108 is that, after implantation, the guide rails 108 also prevent migration of the cage in the medial/lateral/anterior/posterior planes of the segment being fused by having engaged the endplates of the corresponding vertebral bodies. In this manner, an intervertebral body fusion implant device provides for immediate fixation of engaged adjacent vertebrae.

Yet another such advantageous and beneficial result of the guide rail 108 is that they are recessed from the adjacent exterior faces 118 (i.e., outer edges) of the implant device body 102. In this regard, the physical configuration of the guide rails 108 limits the potential for adverse situations if a traumatic injury occurs post operatively and the device 100 does migrate. For example, the guide rails being recessed from the exterior faces 118 provides a "safety zone" in which the device 100 can protrude prior to the guide rails 108 being exposed in vivo. Furthermore, because the guide rails 108 are preferably made from a non-metallic material (e.g., the entire implant device body 102 being made from a polymeric material such as Polyetheretherketone (PEEK)), a bone engagement portion (e.g., upper edge portion) of the guide rails 108 will not be as sharp as a bone engagement portion of a metal device intended to similarly provide immediate fixation in the same type of spine fixation application.

Although the invention has been described with reference to several exemplary embodiments, it is understood that the words that have been used are words of description and illustration, rather than words of limitation. Changes may be made within the purview of the appended claims, as presently stated and as amended, without departing from the scope and spirit of the invention in all its aspects. Although the invention has been described with reference to particular means, materials and embodiments, the invention is not intended to be limited to the particulars disclosed; rather, the invention extends to all functionally equivalent technologies, structures, methods and uses such as are within the scope of the appended claims.

What is claimed is:

1. An intervertebral body fusion implant device configured for being engaged between two adjacent vertebrae, comprising:

an implant device body having an upper bone engaging portion and a lower bone engaging portion, wherein said upper and lower bone engaging portions each include a bone gripping structure configured for limiting relative movement between the implant device body and an engaged one of said adjacent vertebrae and wherein a passage extends through the implant device body between the upper bone engaging portion and the lower bone engaging portion; and a plurality of guide rails extending from each one of said bone engaging portions, wherein the passage extends between a first one and a second one of the guide rails of the upper bone engaging portion and between a first one and a second one of the guide rails of the lower bone engaging portion, wherein at least a portion of each one of the guide rails of each one of said bone engaging portions is exposed above an uppermost portion of the bone gripping structure thereof, and wherein each one of said guide rails is substantially straight and extends parallel with each other one of said guide rails, wherein a bone engaging tip portion of the guide rails at the upper bone engaging portion lie in a first plane, wherein a bone engaging tip portion of the guide rails at the lower bone engaging portion lie in a second plane, wherein the first and second plane extend parallel to each other; and wherein each one of the guide rails has a pointed leading edge and has opposing side faces that converge to form a pointed top edge such that forcible insertion of the intervertebral body fusion implant device between said adjacent vertebrae causes the leading edge of each one of the guide rails to form a guide rail receiving track in a mating endplate surface of a respective engaged one of said adjacent vertebrae as the intervertebral body fusion implant device is being inserted therebetween.

2. The intervertebral body fusion implant device of claim 1 wherein:

the bone gripping structure of each one of said bone engaging portions includes a plurality of protrusions extending from said upper and lower bone engaging portions;

said protrusions are configured for limiting relative movement between the implant device body and an engaged one of said adjacent vertebrae; and the guide rail of each one of said bone engaging portions is unitarily molded with the implant device body such that the implant device body and the guide rail of each one of said bone engaging portions are of a one-piece construction.

3. The intervertebral body fusion implant device of claim 2 wherein:

each one of said protrusions is in the form of a tooth;

a valley is defined between adjacent ones of said protrusions;

a ridge is defined at a tip portion of each one of said protrusions; and the ridge of each one of said protrusions extends substantially parallel to the ridge of each other one of said protrusions.

4. The intervertebral body fusion implant device of claim 3 wherein the ridge of each one of said protrusions extends substantially perpendicular to each one of said guide rails.

5. The intervertebral body fusion implant device of claim 1 wherein:

opposing end portions of the passage define a length of the passage;

the length of the passage is greater than a length of each one of the guide rails; and each one of the guide rails is positioned between opposing end portions of the passage.

6. The intervertebral body fusion implant device of claim 5 wherein:

each one of said guide rails is inwardly offset away from an adjacent exterior side face of the implant device body whereby a space is provided between each one of said guide rails and the adjacent exterior side face of the implant device body;

a length of the implant device body is substantially greater than a length of each one of said guide rails; and each one of said guide rails is positioned such that a space is provided between end portions of each one of said guide rails and an adjacent end face of the implant device body.

7. The intervertebral body fusion implant device of claim 6 wherein:

the implant device body includes a plurality of protrusions extending from said upper and lower bone engaging portions;

said protrusions are configured for limiting relative movement between the implant device body and an engaged one of said adjacent vertebrae;

each one of said protrusions is in the form of a tooth;

a valley is defined between adjacent ones of said protrusions;

a ridge is defined at a tip portion of each one of said protrusions;

the ridge of each one of said protrusions extends substantially parallel to the ridge of each other one of said protrusions; and the ridge of each one of said protrusions extends substantially perpendicular to each one of said guide rails.

8. An intervertebral body fusion implant device configured for being engaged between two adjacent vertebrae, comprising:

an implant device body having an upper bone engaging portion and a lower bone engaging portion, wherein a passage extends through the implant device body between the upper bone engaging portion and the lower bone engaging portion thereby defining opposing side walls of the implant device body and opposing end walls of the implant device body;

a plurality of protrusions extending from said upper and lower bone engaging portions of each one of said side walls; and a guide rail extending from each one of said bone engaging portions of each one of said side walls, wherein the guide rail of each one of said bone engaging portions of each one of said side walls extends beyond a tip portion of each one of said protrusions thereof, wherein each one of said guide rails is substantially straight and extends parallel with each other one of said guide rails and wherein each one of the guide rails has a pointed leading edge and has opposing side faces that converge to form a pointed top edge such that forcible insertion of the intervertebral body fusion implant device between said adjacent vertebrae causes the leading edge of each one of the guide rails to form a guide rail receiving track in a mating endplate surface of a respective engaged one of said adjacent vertebrae as the intervertebral body fusion implant device is being inserted therebetween.

9. The intervertebral body fusion implant device of claim 8 wherein:

each one of said protrusions is in the form of a tooth;

a valley is defined between adjacent ones of said protrusions;

a ridge is defined at a tip portion of each one of said protrusions; and the ridge of each one of said protrusions extends substantially parallel to the ridge of each other one of said protrusions.

10. The intervertebral body fusion implant device of claim 9 wherein the ridge of each one of said protrusions extends substantially perpendicular to each one of said guide rails.

11. The intervertebral body fusion implant device of claim 8 wherein:
opposing end portions of the passage define a length of the passage;
the length of the passage is greater than a length of each one of the guide rails; and
each one of the guide rails is positioned between opposing end portions of the passage.

12. The intervertebral body fusion implant device of claim 8 wherein each one of said guide rails is inwardly offset away from an adjacent exterior side face of the implant device body whereby a space is provided between each one of said guide rails and the adjacent exterior side face of the implant device body.

13. The intervertebral body fusion implant device of claim 12 wherein:
each one of said protrusions is in the form of a tooth;
a valley is defined between adjacent ones of said protrusions;
a ridge is defined at a tip portion of each one of said protrusions;
the ridge of each one of said protrusions extends substantially parallel to the ridge of each other one of said protrusions; and
the ridge of each one of said protrusions extends substantially perpendicular to each one of said guide rails.

14. The intervertebral body fusion implant device of claim 13 wherein:
opposing end portions of the passage define a length of the passage;
the length of the passage is greater than a length of each one of the guide rails; and
each one of the guide rails is positioned between opposing end portions of the passage.

15. An intervertebral body fusion implant device configured for being engaged between two adjacent vertebrae, comprising:
first and second side walls each including an upper bone engaging portion and a lower bone engaging portion;
a plurality of protrusions extending from said upper and lower bone engaging portions of each one of said side walls;
first and second end walls connected between said first and second side walls in a manner providing a passage extending between the upper bone engaging portion of said first and second side walls and the lower bone engaging portion of said side walls; and
a guide rail extending from the upper bone engaging portion of each one of said side walls and a guide rail extending from the lower bone engaging portion of each one of said side walls such that the passage is located between the guide rails of the first side wall and between the guide rails of the second side wall, wherein the guide rail of each one of said bone engaging portions of each one of said side walls extends beyond a tip portion of each one of said protrusions thereof, wherein the guide rail of each one of said bone engaging portions of each one of said side walls is substantially straight and extends parallel with the one or more guide rails of each other one of said bone engaging portions, wherein a bone engaging tip portion of the guide rails at the upper bone engaging portion lie in a first plane, wherein a bone engaging tip portion at the guide rails of the lower bone engaging portion lie in a second plane, wherein the first and second plane extend parallel to each other, and wherein each one of the guide rails has a pointed leading edge and has opposing side faces that converge to form a pointed top edge such that forcible insertion of the intervertebral body fusion implant device between said adjacent vertebrae causes the leading edge of each one of the guide rails to form a guide rail receiving track in a mating endplate surface of a respective engaged one of said adjacent vertebrae as the intervertebral body fusion implant device is being inserted therebetween.

16. The intervertebral body fusion implant device of claim 15 wherein:
each one of said protrusions is in the form of a tooth;
a valley is defined between adjacent ones of said protrusions;
a ridge is defined at a tip portion of each one of said protrusions; and
the ridge of each one of said protrusions extends substantially parallel to the ridge of each other one of said protrusions.

17. The intervertebral body fusion implant device of claim 16 wherein the ridge of each one of said protrusions extends substantially perpendicular to each one of said guide rails.

18. The intervertebral body fusion implant device of claim 15 wherein:
opposing end portions of the passage define a length of the passage;
the length of the passage is greater than a length of each one of the guide rails; and
each one of the guide rails is positioned between opposing end portions of the passage.

19. The intervertebral body fusion implant device of claim 15 wherein each one of said guide rails is inwardly offset away from an adjacent exterior side face of the implant device body whereby a space is provided between each one of said guide rails and the adjacent exterior side face of the implant device body.

20. The intervertebral body fusion implant device of claim 19 wherein:
each one of said protrusions is in the form of a tooth;
a valley is defined between adjacent ones of said protrusions;
a ridge is defined at a tip portion of each one of said protrusions;
the ridge of each one of said protrusions extends substantially parallel to the ridge of each other one of said protrusions; and
the ridge of each one of said protrusions extends substantially perpendicular to each one of said guide rails.

* * * * *